United States Patent [19]
Pagan

[11] Patent Number: 6,019,753
[45] Date of Patent: Feb. 1, 2000

[54] CATHETER ASSEMBLIES AND INNER CANNULAE

[75] Inventor: Eric Pagan, Hythe, United Kingdom

[73] Assignee: Smiths Industries Public Limited Company, London, United Kingdom

[21] Appl. No.: 09/188,064

[22] Filed: Nov. 9, 1998

[30] Foreign Application Priority Data

Dec. 2, 1997 [GB] United Kingdom ............... 9725390

[51] Int. Cl.⁷ .................................................. A61M 25/00
[52] U.S. Cl. ........................................... 604/523; 604/525
[58] Field of Search ..................... 604/164, 264, 604/523–525; 128/200.26, 207.14, 207.15, 207.29, 207.17; 138/173

[56] References Cited

U.S. PATENT DOCUMENTS

| | | | |
|---|---|---|---|
| 4,402,685 | 9/1983 | Buhler et al. .......................... | 604/523 |
| 4,430,083 | 2/1984 | Ganz et al. ............................ | 604/523 |
| 4,919,126 | 4/1990 | Baildon ............................... | 128/207.14 |
| 5,122,125 | 6/1992 | Deuss ................................... | 604/524 |
| 5,125,909 | 6/1992 | Heimberger ........................... | 604/264 |
| 5,386,826 | 2/1995 | Inglis et al. .......................... | 128/207.14 |
| 5,531,671 | 7/1996 | Lundquist et al. . | |
| 5,873,362 | 2/1999 | Parker ................................. | 128/207.14 |
| 5,882,347 | 3/1999 | Mouris-Laan et al. . | |

FOREIGN PATENT DOCUMENTS

| | | |
|---|---|---|
| 0 689 851 | 1/1996 | European Pat. Off. . |
| 2044109 | 10/1980 | United Kingdom . |
| 2323534 | 9/1998 | United Kingdom . |
| WO 96/40339 | 12/1996 | WIPO . |
| WO 97/27895 | 8/1997 | WIPO . |

*Primary Examiner*—John D. Yasko
*Attorney, Agent, or Firm*—Pollock, Vande Sande & Amernick

[57] ABSTRACT

A tracheostomy tube assembly has an outer catheter and an inner cannula that is insertable into and removable from the outer catheter. The inner cannula has two elongate regions along its length of different flexibility. The main body of the cannula may be relatively stiff and a narrow region along its length be of a more flexible material, such as extruded to form the entire thickness of the wall of the cannula, so that the cannula is preferentially flexible in the plane of the center line of the narrow region to permit the cannula to be inserted, without kinking or buckling, into the outer catheter.

11 Claims, 2 Drawing Sheets

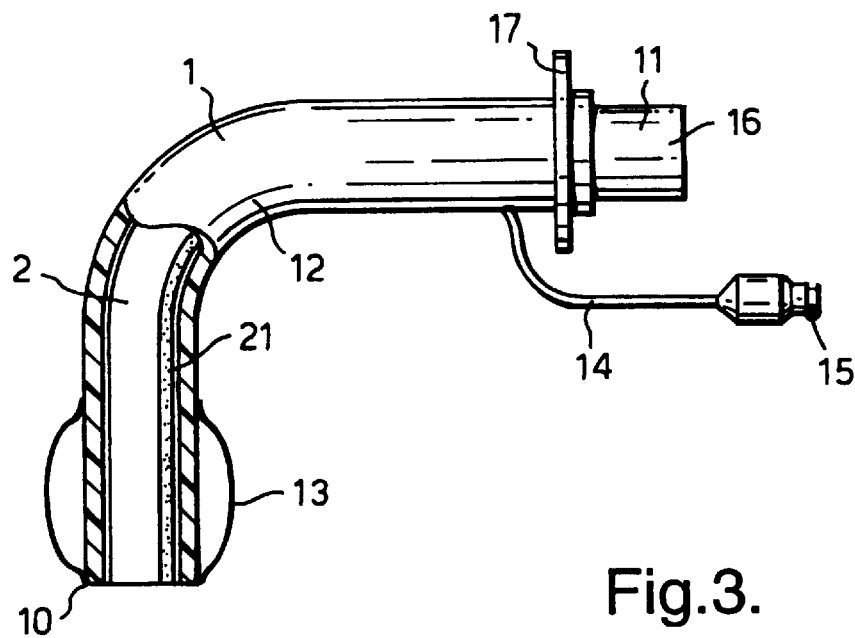
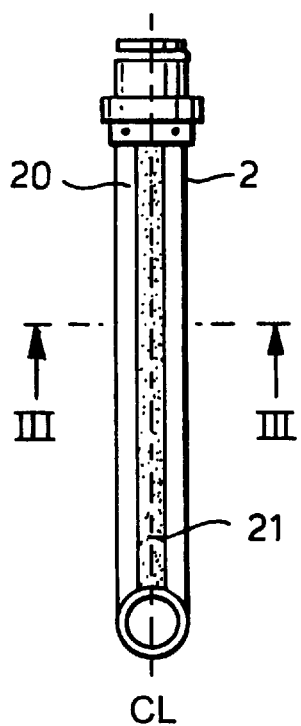
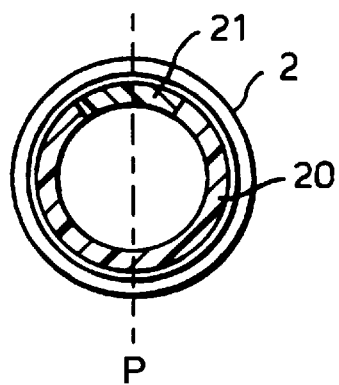
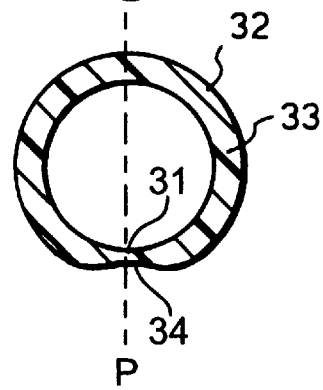

CATHETER ASSEMBLIES AND INNER CANNULAE

BACKGROUND OF THE INVENTION

This invention relates to catheter assemblies and to inner cannulae for such assemblies.

The invention is more particularly concerned with catheter assemblies having a catheter and a removable inner cannula.

Some catheter assemblies, such as tracheostomy tubes, have an inner cannula, which is removable from the catheter. By removing and replacing the inner cannula, the secretions that build up within the catheter can be removed without the need to replace the catheter itself. This can reduce the risk of infection and, by avoiding the need to remove the catheter, it can reduce the discomfort, disturbance and trauma caused to the patient.

Although an inner cannula can have advantages, it can reduce the flow through the catheter because of the smaller internal diameter of the inner cannula. Thus, it is desirable that the wall of the inner cannula be as thin as possible and that it be a close fit within the catheter. Where the tracheostomy tube is of a radial shape, that is, it is curved along its entire length, the inner cannula can be similarly shaped so it does not need to bend during insertion, thereby enabling it to be relatively rigid. It is preferable, however, in some cases to use a tracheostomy tube with an anatomical design, in which opposite ends of the tube are relatively straight and linked by a curved section midway. With such a tube, the inner cannula must be able to flex as it is inserted and removed. If, however, the wall thickness of the inner cannula is simply reduced to increase flexibility, the cannula may tend to buckle during insertion and may cause a restriction in flow. To prevent buckling, a cannula may be used that is corrugated around its entire circumference but these corrugations can impede gas flow along the catheter appreciably as a result of the reduction in internal diameter and turbulence.

In GB 2319183 there is described an inner cannula having a series of slots through its wall, which are covered by a thin, flexible sheath applied to the inner surface of the cannula. EP 215173 describes a catheter with notches in its wall filled with softer material.

BRIEF SUMMARY OF THE INVENTION

It is an object of the present invention to provide an improved catheter assembly and inner cannula.

According to one aspect of the present invention there is provided a cannula comprising a tubular member, the tubular member having two elongate regions extending along its length, the two regions having different flexibilities such that the cannula is preferentially flexible in the plane of the center line of the region of greater flexibility.

The main body of the tubular member is preferably of a relatively stiff material, the cannula having a narrow elongate region extending along the length of the cannula of a more flexible material. The narrow region may extend through the entire thickness of the wall of the tubular member. Alternatively, the region of greater flexibility may be provided by a region of reduced wall thickness or by a region having a series of part-circumferential corrugations. Alternatively, the main body of the cannula may be of a relatively flexible material, the cannula having a narrow elongate region extending along the length of the cannula of a stiffer material or a stiffer narrow elongate region provided by a rib of the same material. The cannula may be bent along its length in the plane and may be made by extrusion. The cannula may be held against a corrugated former before it has fully cured.

According to another aspect of the present invention there is provided a method of making a cannula including the steps of extruding a tubular member with two elongate wall regions of materials of different flexibility, and bending the extruded member before it has fully cured in the plane of a center line of the region of more flexible material.

According to a further aspect of the present invention there is provided a cannula made by a method according to the above other aspect of the invention.

A tracheostomy tube assembly including various different inner cannulae according to the present invention, will now be described, by way of example, with reference to the accompanying drawings.

BRIEF DESCRIPTION OF THE DRAWINGS

FIG. 1 is a partly cut-away side elevation view of the assembly with a first form of inner cannula;

FIG. 2 is a side elevation view of the inner cannula of FIG. 1;

FIG. 3 is a transverse cross-sectional view of the cannula along the line III—III of FIG. 2, to an enlarged scale;

FIG. 4 is a transverse cross-sectional view of a second form of inner cannula;

DETAILED DESCRIPTION OF THE PREFERRED EMBODIMENTS

Figure 5:
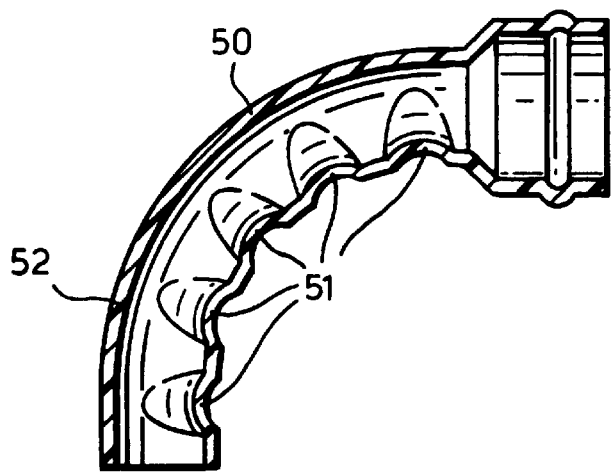
FIG. 5 is a sectional side elevation view of a third form of inner cannula.

With reference to FIG. 1, the catheter assembly comprises a tracheostomy tube or catheter 1 and an inner cannula 2 within the tracheostomy tube.

The tracheostomy tube 1 is of a conventional form, having a patient end 10 and a machine end 11, which extends at right angles to the patient end 10. In use, the patient end 10 is located in the trachea and the machine end 11 projects from a surgically-made opening in the neck of the patient. The tube 1 has an internal diameter between 3–11 mm. The patient end 10 and machine end 11 are substantially straight and are interconnected by an intermediate, curved region 12 so that the tube substantially complies with the patient's anatomy. An inflatable cuff 13 encircles the tube 1 close to its patient end 10 and is inflatable via an inflation line 14 and connector 15. The inflatable cuff 13 is not essential since many tracheostomy tubes do not have such a cuff. The machine end 11 of the tube 1 has a connector 16 and a flange 17, which enables the tube to be held in position on the patient's neck.

With reference now also to FIGS. 2 and 3, the inner cannula 2 has a tubular member 20 of circular section and an external diameter slightly less than the internal diameter of the tube 1. The tubular member 20 is preformed to the same approximate shape as the tube 1, that is, it has a bend of approximately right angles. The wall of the tubular member 20 is primarily of a relatively stiff plastics material, such as PVC, polythene, polypropylene, nylon or fluoropolymer, apart from an elongate region 21 extending longitudinally along the entire length of the tubular member along the inside of its curve. This elongate region 21 is of a more flexible plastics material than the main part of the tubular member 20, such as softer grades of PVC or polythene, EVA or TPE. The more flexible region 21 is shown as extending through the entire thickness of the wall of the member 20 but it could only occupy a part of the thickness. Typically, the wall thickness of the tubular member 20 is between about 0.3 to 0.6 mm. The flexible region 21 can be made by coextruding at the same time as the main part of the tubular member 20. The flexible region 21 makes the tubular member 20 preferentially flexible in the plane P of the center line CL of the flexible region, that is, the plane including the axis of the tube and a line extending along the center of the length of the flexible region so that it can flex readily during insertion of the cannula 2 into the outer tube 1 and during removal from the outer tube. The cannula 2, however, maintains its axial rigidity, that is, it does not contract when pushed, or expand when pulled. The rigidity is sufficient to enable the cannula 2 to be pushed into the outer tube 1 with sufficient force to overcome the friction with the tube and without kinking or buckling.

The elongate region need not be of a different material, a region of increased flexibility could be provided by a region 31 of reduced wall thickness, as shown in FIG. 4. In this inner cannula 32, the tubular member 33 is made of the same material and the region 31 of reduced thickness is formed by a groove 34 extending longitudinally along the outside of the tubular member. Again, this region 31 is provided along the inside curve of the cannula 32.

In an alternative embodiment shown in FIG. 5, the wall of the cannula 50 is continuous and of the same material but it is made preferentially flexible by forming a series of corrugations 51 along an elongate region extending along the inside curve of the cannula. The corrugations 51 take the form of shallow indentations in the tubular wall 52 of the cannula and extend around only a part of the circumference of the wall, typically about one half its circumference. The depth of the corrugations 51 is about equal to the wall thickness, that is, the corrugations are recessed by about 0.3 to 0.4 mm below the outside surface of the wall. The tubular wall 52 of the cannula 50 is preformed with a bend of the same shape as that of the outer tube 1 and has a constant wall thickness, even in the region of the corrugations 51. The corrugations 51 enable the cannula 50 to flex more readily in the plane of curvature, that is, in the plane P including the center line CL of the series of corrugations and the axis of the cannula. Because the corrugations 51 extend along only the inside of the curve, there is little impediment to insertion of a suction catheter, which would normally only contact the outside of the curve at its tip. Also, there is less turbulence than with a cannula that is corrugated around its entire circumference. A region of the cannula, such as its patient end tip, could be made more flexible than the remainder of the cannula by increasing the length of the corrugations, that is, so that they extend further around the cannula, or by reducing the pitch or separation of the corrugations.

Figure 6:
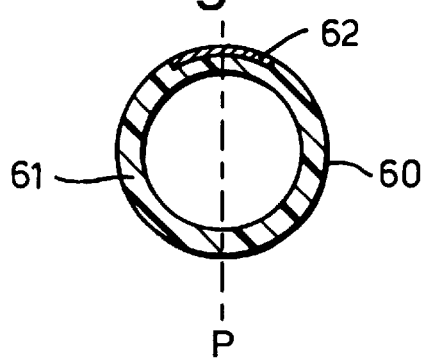
FIG. 6 is a transverse cross-sectional view of a fourth form of inner cannula.

The cannula could, alternatively, be made preferentially flexible in one plane by providing it with a more rigid elongate region, rather than a more flexible region. In the arrangement shown in FIG. 6, the cannula 60 has a tubular wall 61, such as of PEBA, nylon or FEP in which a strip 62 is coextruded of a material more rigid than the remainder of the wall, such as nylon, PES or an aramid, such as Kevlar. In cross-section, the strip 62 has a width or circumferential dimension that exceeds its thickness, so that the strip is more flexible in a plane P including the center line CL along the length of the strip and at right angles to its width, than in a plane including the width of the strip. The strip 62 is located along the outside or inside of the curve of the cannula 60 so that the cannula is rendered more flexible in the plane P of the curvature than at right angles to this. The thickness of the wall 61 may be increased in the region of the strip 62, such as to a thickness 1.5 times that opposite the strip.

Figure 7:
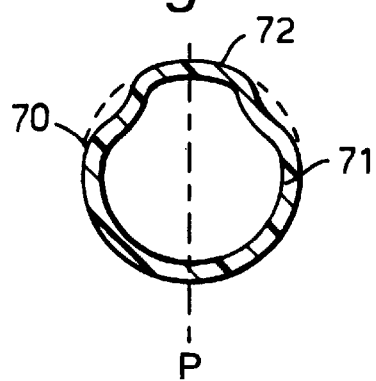
FIG. 7 is a transverse cross-sectional view of a fifth form of inner cannula.

A similar reinforcement could be provided in the manner shown in FIG. 7 by forming a rib or spine 72 along the length of the tubular wall 71 of a cannula 70. The rib 72 has the same wall thickness as the remainder of the wall 71 and projects above the remainder of the wall by a distance approximately equal to the wall thickness. The width of the rib 72 is about four times its height so, again, it is preferentially flexible in a longitudinal plane P at right angles to the width along a center line CL extending longitudinally, centrally of the rib. The rib 72 is formed along the inside or outside of the curve of the cannula 70.

Figure 8:
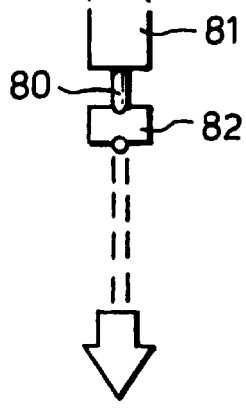
FIGS. 8 to 10 illustrate steps in manufacture of an inner cannula.
Figure 9:
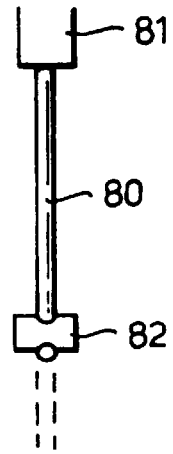
Figure 10:
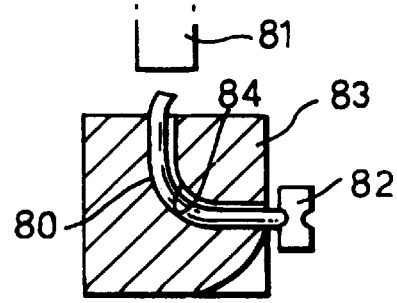

With reference now to FIGS. 8 and 9, the tubular wall of the cannula may be made by extruding a straight length of tubing 80 from an extruder head 81, the end farthest from the head being retained by a holder 82. When the desired length has been extruded, a former 83 is brought up to the extruder head, the former 83 (FIG. 10) having a convex forming surface 84 shaped to the desired inside curve of the cannula. The holder 82 is swung to one side to hold the length of extruded tubing 80 against the forming surface 84. The tubing is held in the former 83 while it is warm and still curing so that it takes on the shape of the forming surface 84. The tubing 80 may be severed from the extruder head 81 either before or after it has been fully cured. The former 83 could be shaped to form corrugations or other surface formations or textures on the outer surface of the tubular wall.

The flexibility of the inner cannula 2 enables it to bend readily to comply with the shape of the outer tube 1, when the plane of flexibility of the cannula is aligned with the plane P of curvature of the outer tube, even though the catheter has two straight regions separated by a curved region. The axial rigidity of the cannula means that it can be inserted within the outer catheter without any danger of the cannula collapsing axially, like a concertina. The inside of the cannula can have a relatively smooth surface, thereby reducing gas turbulence and enabling a suction catheter, cleaning brush or other device to be inserted without snagging.

The inner cannula is not confined to tracheostomy tube assemblies but could be used in other assemblies having an outer catheter and an inner cannula.

What I claim is:

1. A catheter assembly comprising an outer catheter and an inner cannula extending within the outer catheter, the outer catheter being preformed with a curve along its length in a plane, the inner cannula comprising a flexible tubular member having two elongate regions extending along its length, said two regions having different flexibilities such that the cannula is preferentially flexible in a plane including the axis of the cannula and a center line extending centrally along the length of one of said elongate regions, the inner cannula being inserted in the outer catheter with the plane of curvature of the outer catheter coincident with the plane of preferential flexibility of the inner cannula.

2. An assembly according to claim 1, wherein said regions extend through the entire thickness of a wall of the tubular member.

3. An assembly according to claim 1, wherein one of said two regions has greater flexibility than the other of said two regions, said region of greater flexibility being provided by a region of reduced wall thickness.

4. An assembly according to claim 1, wherein the one of said two regions having greater flexibility than the other of said two regions is provided by a series of part-circumferential corrugations in said tubular member.

5. An assembly according to claim 1, wherein the cannula has a main body of a relatively flexible material, and wherein the cannula has a narrow elongate region extending along the length of the cannula of a stiffer material.

6. An assembly according to claim 1, wherein the cannula has a main body of a relatively flexible material, and wherein the cannula has a stiffer narrow elongate region provided by a rib of the same material as the main body.

7. An assembly according to claim 1, wherein the cannula is bent along its length in said plane.

8. An assembly according to claim 1, wherein the cannula is made by extrusion.

9. An assembly according to claim 5, wherein the cannula is made by extrusion and by holding the extruded cannula against a corrugated former before it has fully cured.

10. An assembly according to claim 1, wherein said two regions are of different materials.

11. An assembly comprising an outer catheter and an inner cannula insertable into and removable from said catheter, said cannula comprising a tubular member having a main body of a relatively stiff plastics material, said tubular member also having an elongated strip of a more flexible material extending longitudinally along said main body such that the cannula is preferentially flexible in a plane of a center line of the elongated strip.

* * * * *